United States Patent
Seshimoto et al.

[11] Patent Number: 5,928,951
[45] Date of Patent: Jul. 27, 1999

[54] FRAMELESS CHEMICAL ANALYSIS FILM CLIP

[75] Inventors: Osamu Seshimoto; Yoshihiko Abe; Yasushi Fujisaki, all of Saitama-ken, Japan

[73] Assignee: Fuji Photo Film Co., Ltd., Kanagawa-ken, Japan

[21] Appl. No.: 08/883,265

[22] Filed: Jun. 26, 1997

Related U.S. Application Data

[63] Continuation of application No. 08/691,226, Aug. 1, 1996, abandoned, which is a continuation of application No. 08/591,904, Jan. 25, 1996, abandoned, which is a continuation of application No. 08/269,033, Jun. 30, 1994, abandoned.

[30] Foreign Application Priority Data

Jul. 16, 1993 [JP] Japan ................................ 5-177054

[51] Int. Cl.⁶ ........................... G01N 35/10; G01N 21/77
[52] U.S. Cl. .................. 436/46; 436/43; 436/164; 436/169; 436/170; 422/56; 422/57; 422/63; 422/66
[58] Field of Search ................... 422/56–58, 60, 422/63, 66; 436/43, 46, 805, 164, 169, 170

[56] References Cited

U.S. PATENT DOCUMENTS

| | | | |
|---|---|---|---|
| 3,992,158 | 11/1976 | Przybylowicz et al. | 422/57 |
| 4,258,001 | 3/1981 | Pierce et al. | 422/56 |
| 4,292,272 | 9/1981 | Kitajima et al. | 422/57 |
| 4,783,315 | 11/1988 | Arai et al. | 422/56 |
| 4,870,005 | 9/1989 | Akiyoshi et al. | 435/7 |
| 5,019,347 | 5/1991 | Hiratsuka et al. | 422/56 |
| 5,120,506 | 6/1992 | Saito et al. | 422/66 |
| 5,336,599 | 8/1994 | Kitajima | 435/15 |

FOREIGN PATENT DOCUMENTS

| | | |
|---|---|---|
| 0064691 | 11/1982 | European Pat. Off. . |
| 0 162 302 | 11/1985 | European Pat. Off. . |
| 0162302 | 11/1985 | European Pat. Off. . |
| 0 226 465 | 6/1987 | European Pat. Off. . |
| 0525550 | 2/1993 | European Pat. Off. . |
| 0555654 | 8/1993 | European Pat. Off. . |
| 47-37993 | 2/1972 | Japan . |
| 49-53888 | 5/1974 | Japan . |
| 57-125847 | 5/1982 | Japan . |
| 57-148250 | 9/1982 | Japan . |

*Primary Examiner*—Long V. Le
*Attorney, Agent, or Firm*—McAulay Nissen Goldberg Kiel & Hand, LLP

[57] ABSTRACT

A chemical analysis film chip is prepared by integrally laminating a reagent layer and a spreading layer on a support sheet in this order, or by integrally laminating a water absorbing layer having a hydrophilic polymer as a major component and a porous outermost layer containing therein a reagent on a support sheet in this order, or by superposing a porous layer containing therein a reagent on a support sheet.

25 Claims, 6 Drawing Sheets

FRAMELESS CHEMICAL ANALYSIS FILM CLIP

This is a continuation of application Ser. No. 08/691,226, filed Aug. 1, 1996, now abandoned, which, in turn, is a continuation of application Ser. No. 08/591,904, filed Jan. 25, 1996, now abandoned, which, in turn, is a continuation of application Ser. No. 08/269,033, filed Jun.30, 1994, now abandoned.

BACKGROUND OF THE INVENTION

1. Field of the Invention

This invention relates to a chemical analysis film chip having a reagent layer whose optical density changes upon reaction with a specific biochemical component contained in a sample liquid such as blood or urine.

2. Description of the Prior Art

Quantitative or qualitative analysis of a specific component in a sample liquid is a common operation carried out various industrial fields. Especially, quantitative analysis of a chemical component or a solid component contained in body fluid such as blood or urine is very important in the field of clinical biochemistry.

There has been put into practice a "dry-to-the-touch" (to be expressed simply as "dry" hereinbelow) chemical analysis slide with which a specific component contained in a sample liquid can be quantitatively analyzed through a droplet of the sample liquid spotted onto the slide. See Japanese Patent Publication No. 53(1978)-21677, U.S. Pat. No. 3,992,158, Japanese Unexamined Patent Publication No. 55(1980)- 164356, U.S. Pat. No. 4,292,272 or the like. When such a dry chemical analysis slide is used, the sample liquid can be analyzed more easily and more quickly than when the conventional wet analysis method is used, and accordingly the dry chemical analysis slide is very convenient for medical facilities, laboratories and the like where lots of sample liquids have to be analyzed.

When chemical components or the like contained in a sample liquid is analyzed using such a dry chemical analysis slide, a droplet of the sample liquid is spotted onto the slide and is held at a constant temperature for a predetermined time (incubation) in an incubator so that coloring reaction occurs, and the optical density of the color formed by the coloring reaction is optically measured. That is, measuring light containing a wavelength which is pre-selected according to the combination of the component to be analyzed and the reagent contained in the reagent layer of the slide is projected onto the slide and the optical density of the slide is measured. Then the component to be analyzed is quantitatively analyzed on the basis of the optical density using a calibration curve which represents the relation between the concentration of the biochemical component and the optical density.

The chemical analysis slide comprises a dry chemical analysis film and a plastic frame which holds the chemical analysis film flat to facilitate handling of the film during transfer. The chemical analysis film is generally composed of a support sheet of plastic or the like and a reagent layer and a spreading layer superposed on the support sheet or of a support sheet and a water absorbing layer having hydrophilic polymer as a major component and a spreading layer containing therein a reagent which are superposed on the support sheet.

The chemical analysis slides are transferred to an incubator one by one after spotted with a sample liquid. Generally the incubator has a plurality of cells for accommodating the chemical analysis slides. Each cell is in the form of a slit (or a flat room) which opens in the side of the incubator and the chemical analysis slides are inserted into the cells. Such transfer of the chemical analysis slides can be done, for instance, by a reciprocating claw member as disclosed in U.S. Pat. Nos. 4,296,069 and 4,568,519 and the like. The frame facilitates transfer of the chemical analysis film.

However, use of such chemical analysis films with frame results in increase in the size of various parts handling the films such as cells in the incubator for incubating the chemical analysis films, the transfer system, a film supplier for storing the films in dry state and the like. Thus the frame of the chemical analysis film is obstructive to reducing the size of the biochemical analysis system and at the same time reduces the film accommodating capacity of the incubator, which obstructs increase in handling capability of the overall biochemical analysis system.

Further cost for mounting the frame is high, which adds to cost of biochemical analysis.

SUMMARY OF THE INVENTION

In view of the foregoing observations and description, the primary object of the present invention is to provide a dry chemical analysis film without frame (will be referred to as "chemical analysis film chip", hereinbelow) which can be used instead of the chemical analysis slide in a biochemical analysis system, thereby reducing the size of various parts of the biochemical analysis system to miniaturize the overall biochemical analysis system and reducing the cost of biochemical analysis as compared with the biochemical analysis system using chemical analysis films with frame (chemical analysis slides).

The dry chemical analysis film chip in accordance with the present invention is for use in an automated biochemical analysis system. In accordance with one aspect of the present invention, the chemical analysis film chip is essentially composed of a support sheet and a reagent layer and an outermost layer superposed on the support sheet in this order and is characterized in that it curves (or warps or curls) at random in a dry atmosphere. In accordance with another aspect of the present invention, the chemical analysis film chip is essentially composed of a support sheet and a water absorbing layer having a hydrophilic polymer as a major component and a spreading layer containing therein a reagent which are superposed on the support sheet and is characterized in that it curves at random in a dry atmosphere. In accordance with still another aspect of the present invention, the chemical analysis film chip is essentially composed of a support sheet and a porous layer containing therein a reagent superposed on the support sheet and is characterized in that it curves at random in a dry atmosphere.

It is preferred that the support sheet has a strength to permit transfer of the chemical analysis film chip while holding it under a suction force.

In order to stably and surely take out such curved chemical analysis film chips from a cartridge and transfer them, it is necessary to flatten the films or to correct the curves of the films to be uniform. For this purpose, it is preferred that the support sheet, the water absorbing layer, the reagent layer and the outermost layer are all strong enough to withstand a suction force acting on the film chip during transfer thereof without being damaged even if they are bent by the suction force, i.e., without producing crack, fracture or separation between the layers.

It is preferred that the outermost layer be a spreading layer.

Preferably the outermost layer, the porous layer containing therein the reagent or the spreading layer should withstand to rubbing with the member handling the film chip or with the support sheet of another film chip.

Preferably the outermost layer, the porous layer containing therein the reagent or the spreading layer should be of fabric (cloth) or paper.

That the chemical analysis film chip of this embodiment is essentially composed of the support sheet and the layer(s) identified above means that the film chip is not provided with frame unlike the chemical analysis slide described above.

The term "dry atmosphere" means an atmosphere where humidity is largely lower than the normal humidity, e.g., having a humidity of not higher than 20%.

Though the reagent contained in the reagent layer, the spreading layer, the porous layer or the like does not react without existence of water, it can begin reacting as soon as it absorbs moisture. Accordingly, if the reagent is brought into contact with water before analysis, the result of measurement cannot be precise. So the chemical analysis film chips are stored in a dry atmosphere until it is spotted with a sample liquid. In this state, the film chip curves into a roof tile shape.

Figure 1A:
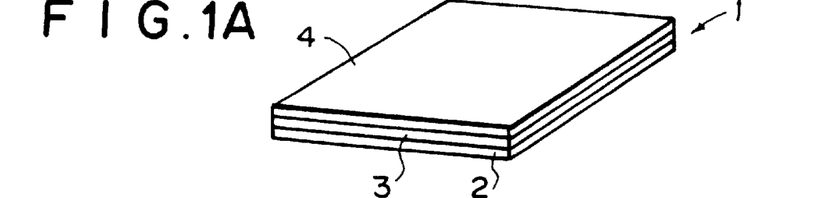
FIG. 1A is a perspective view showing a dry chemical analysis film chip in accordance with an embodiment of the present invention under the normal humidity condition.
Figure 1B:
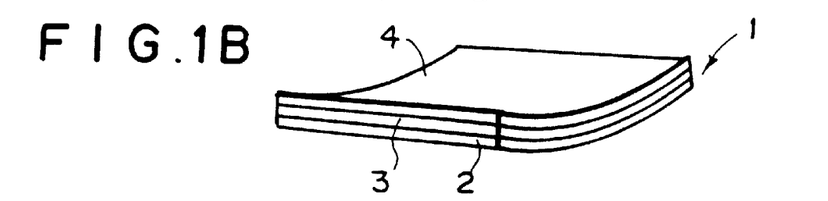
FIGS. 1B and 1C are perspective views showing the dry chemical analysis film chip in a dry state.
Figure 1C:
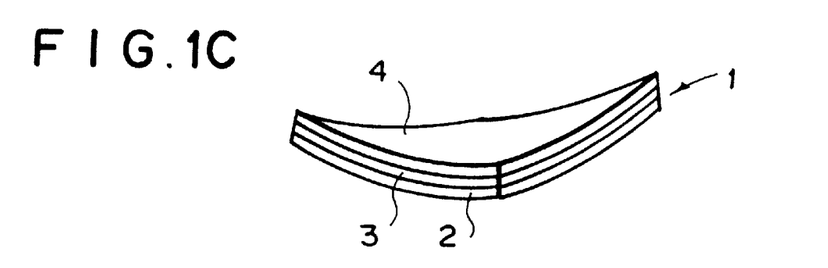

That the chemical analysis film chip curves at random means does not simply means whether the film chip is concave upward or downward but means that it curves in various directions in the manner shown in FIGS. 1B and 1C.

That the outermost layer, the porous layer or the spreading layer should withstand to rubbing with the member handling the film chip or with the support sheet of another film chip means that the layer should have a predetermined resistance to wear, resistance to impact and surface slipperiness and cannot scratch the support sheet of the adjacent film chip when a plurality of film chips are stacked. The "predetermined resistance to wear" is such a resistance which the layer should have not to be damaged by the support sheet of the adjacent film chip when each film chip is drawn out from a cartridge in which a plurality of film chips are stacked.

The "predetermined resistance to impact" is such a resistance which the layer should have not to be damaged by impact and/or load when the upper and lower sides of the film chip are simultaneously brought into contact with upper and lower edges of an opening of said cartridge through which the film chip is drawn out from the cartridge and by impact due to rubbing with the adjacent film chip. Further the outermost layer and the like should have such an elasticity that it can contract in the direction of its thickness according to the load upon receipt of such an impact and can recover its original thickness in a few seconds thereafter. Such an elasticity is included in said predetermined resistance to impact.

The "predetermined surface slipperiness" is such properties which the layer should have to prevent damage on the outermost layer or the like when the upper surface of one film chip slides on the lower side of the film chip adjacent thereto during drawing the film chip from the cartridge.

The dry chemical analysis film chip in accordance with the present invention is for one analysis of a sample liquid and is generally obtained by cutting a dry chemical analysis film roll in a continuous length into chips of predetermined share.

Basically the chemical analysis film chip of this invention is prepared by integrally laminating a reagent layer and a spreading layer on a support sheet in this order, or by integrally laminating a water absorbing layer having a hydrophilic polymer as a major component and a spreading layer containing therein a reagent on a support sheet in this order, or by superposing a porous layer containing therein a reagent on a support sheet as described above.

It is preferred that the support sheet be transmissive to light. For this purpose, it is preferred that the support sheet be formed of a transparent material such as organic polymers, e.g., polyethylene terephthalate, polystyrene and acrylic polymers, such as polymethyl methacrylate. The thickness of the support sheet is within a range of about 100 $\mu$m to about 1000 $\mu$m, and preferably within a range of about 150 $\mu$m to about 300 $\mu$m.

The support sheet may be of any shape and any size. For example, the support sheet may be square, rectangular or circular, and is generally of the same shape as the reagent layer. The support sheet may be equal to, larger than or smaller than the reagent layer.

The water absorbing layer contains therein as a major component a hydrophilic polymer which absorbs water to swell. The hydrophilic polymer used for the water absorbing layer is the similar to that used for the reagent layer. The water absorbing layer absorbs water contained in the sample liquid spotted onto to the spreading layer superposed on the water absorbing layer and assists the sample liquid to be spread in the spreading layer and to reach inside the spreading layer, thereby assisting the analyte (the biochemical component in the sample liquid to be quantitatively analyzed) to contact with the reagent in the spreading layer. An additional water absorbing layer may be provided under the reagent layer.

The reagent layer is formed of at least one layer composed of a hydrophilic polymer binder such as gelatin, polyacrylamide or polyvinyl alcohol containing therein a reagent component which directly or indirectly (through a pre-reaction) makes a coloring reaction (a coloring matter forming reaction) or a discoloring reaction with the analyte through which the analyte is quantitatively analyzed. The coloring or discoloring reaction includes a chemical, a biochemical reaction and an immunoreaction. In the case of a dry chemical analysis film chip for quantitatively analyzing hemoglobin or the like, the hydrophilic polymer binder need not contain a reagent component.

The spreading layer may be formed of known fibrous or non-fibrous microporous materials. Examples of the spreading layer include fibrous porous spreading layers such as woven fabric spreading layers (e.g., plain weave fabrics such as velvet and poplin) disclosed in Japanese Unexamined Patent Publication Nos. 55(1980)-164356 and 57(1982)-66359 and U.S. Pat. Nos. 4,292,272 and 4,783,315, knitted fabric spreading layers (e.g., tricot knitted fabric, double tricot knitted fabric and milanese knitted fabric) disclosed in Japanese Unexamined Patent Publication No. 60(1985)-222769 and European Patent No. 162,302A), organic-polymer-fiber-pulp-filled paper (paper containing organic-polymer-fiber-pulp made by paper making process) spreading layers disclosed in Japanese Unexamined Patent Publication No. 57(1982)148250, and spreading layers formed by coating dispersion of fibers and hydrophilic polymer disclosed in Japanese Unexamined Patent Publication No. 57(1982)-125847; non-fibrous isotropically porous spreading layers such as membrane filters (blushed polymer layer) disclosed in Japanese Patent Publication No. 53(1978)-21677 and U.S. Pat. No. 3,992,158, interconnected-pore isotropic microporous spreading layers having fine particles of polymer micro-beads or the like bonded in spot contact thereon with a hydrophilic polymer binder, and interconnected-pore isotropically microporous spreading layers (three-dimensional lattice particulate structure layer) having polymer micro-beads bonded in spot contact thereon with a hydrophilic polymer adhesive which does not swell with water disclosed in Japanese Unexamined Patent Publication No. 55(1980)-90859 and U.S. Pat. No. 4,258,001; and spreading layers obtained by laminating a plurality of microporous layers (e.g., a knitted or woven fabric layer and a membrane filter layer; a knitted or woven fabric layer and a membrane filter layer and a knitted or woven fabric layer) with adhesive interposed between the layers in a pattern of fine dots or islands (like intaglio gravure or halftone dots in the field of printing) (these spreading layers are excellent in blood cell separation) disclosed in Japanese Unexamined Patent Publication Nos. 61(1986)-4959, 62(1987)-138756, 62(1987)-138757, 62(1987)-138758, U.S. Pat. No. 5,019,347 and European Patent No. 226,465A).

As the porous layer containing therein a reagent may be formed of porous material used for the spreading layer.

Generally filter paper made by paper making process is used.

The chemical analysis film chip of the present invention is generally square, rectangular, circular or oval in shape. In the case of a square or rectangular chemical analysis film chip, the length of one side is generally in the range of about 5 mm to about 20 mm and the thickness is in the range of about 200 $\mu$m to about 2.0 mm. In the case of a circular chemical analysis film chip, the diameter is generally in the range of about 5 mm to about 20 mm and the thickness is in the range of about 200 $\mu$m to about 2.0 mm. In the case of an oval chemical analysis film chip, the major and minor axes are generally in the range of about 5 mm to about 20 mm and the thickness is in the range of about 200 $\mu$m to about 2.0 mm. From the view point of easiness of manufacture and handling in analysis, it is preferred that the film chip is of square or of rectangle whose sides are substantially equal to each other in length.

Preferably the support sheet, the reagent layer and the spreading layer are of the same size and the support sheet and the reagent-containing porous layer are of the same size.

Preferably the chemical analysis film chip should have flexibility to withstand bending and stretching.

That is, when the chemical analysis film chip is drawn out from a cartridge it is formed into a curled state, and when the optical density is measured, the chemical analysis film chip is held flat in the cell of the incubator. If crack, nick or peeling is produced in the film chip, or fatigue remains in the film chip, the sample liquid cannot be uniformly developed or the optical properties of the film chip changes (e.g., part of the film chip becomes opaque), which adversely affects the accuracy of analysis.

For example, the following biochemical components can be quantitatively analyzed with the chemical analysis film chip of the present invention. Blood sugar (glucose), cholesterol, urea nitrogen (BUN), creatinine, bilirubin, hemoglobin, GOT (glutamic-oxaloacetic transaminase), GPT (glutamic acid pyruvic acid transferase), amylase, and C-reactive protein (CRP).

As described above the chemical analysis film chip comprises a support sheet and a reagent layer and an outermost layer superposed on the support sheet in this order, or a support sheet and a water absorbing layer having a hydrophilic polymer as a major component and a spreading layer containing therein a reagent which are superposed on the support sheet in this order or a support sheet and a reagent-containing porous layer superposed on the support sheet, and is not provided with a frame.

Since the chemical analysis film chip of this embodiment has no frame, it may be smaller in the outer dimensions as compared with the conventional chemical analysis slide.

Accordingly, the cartridge for storing a large number of film chips and the drying container (supplier) for storing a plurality of cartridges can be smaller in size as compared with those for the chemical analysis slides. Further the incubator for incubating the film chips spotted with sample liquid as well as the transfer system for transferring the film chips from the cartridge to the incubator can be smaller in size. Thus the overall biochemical analysis system can be made substantially smaller. Further the number of film chips which can be stored in a given size of cartridge or drying container and the number of film chips which can be incubated in a given size of incubator can be increased, whereby the throughput capacity of the biochemical analysis system can be increased.

Further, though a large number of chemical analysis film chips are stored in the cartridge and a plurality of cartridges are stored in the drying container, the drying efficiency can be higher since it is not required to dry the frames unlike in those for the chemical analysis slides.

The cost for producing and mounting the frame can be saved, and the cost of biochemical analysis can be lowered.

Since the chemical analysis film chip of the present invention is apt to suffer damage during transfer due to its frameless structure, it is preferred that the film chip be transferred by use of suction holding means such as a suction pad. In such a case, the suction force applied to the suction holding means should be adjusted so that the dry chemical analysis film chips can be taken out one by one from the cartridge in the drying container, can be transferred to the desired position in the cells in the incubator while kept in place for example upon spotting of sample liquid and can be taken out from the incubator.

Accordingly when the support sheet has a strength suitable for transfer of the film chip by use of such a suction holding means, the film chip can be smoothly taking out from the cartridge, transferred to the cell in the incubator and discharged from the incubator.

When the film chips are taken out from the cartridge in which a number of film chips are stacked, a suction pad is brought into contact with the lowermost chip, for instance, through an opening formed in the bottom of the cartridge and is moved laterally to move the film chip outside the cartridge through a film takeout slit formed in one side wall of the cartridge. As described above, the film chips are curved in the dry state and the curvature finely varies from chip to chip. The film takeout slit should have such a size that only one film chip (the lowermost chip) can pass therethrough.

Accordingly, when the support sheet has an enough strength not to be damaged even if it is curved in order to hold it under a suction force, it is possible to curve each film chip to be convex downward and to form the film takeout slit into a shape conforming to the cross-sectional shape of the film in such a curved state. In this manner, the film chips stored in the cartridge can be smoothly taken out one by one without damage.

Since the chemical analysis film chip of the present invention has no frame, its surfaces are directly rubbed with other members or other film chips during handling.

Accordingly when the outermost layer, the reagent-containing porous layer or the spreading layer are strong enough to withstand to rubbing, for instance, when the layers are formed of fabric or paper, biochemical analysis can be effected stably without causing a problem of layer dropping which takes place, for instance, in the chemical analysis element disclosed in Japanese Unexamined Patent Publication No. 49(1974)-53888 where the element comprises a blushed polymer containing therein fine particles of titanium dioxide.

Chemical analysis elements somewhat similar to the chemical analysis film chip of this embodiment are disclosed in Japanese Unexamined Patent Publication Nos. 47(1972)-37993 and 49(1974)-53888.

The chemical analysis element disclosed in the former publication is a test chip for semi-quantitative analysis which comprises a base portion, reagent layer and a screen-like coating. The screen-like coating is provided for the purpose of suppressing influence of environment such as moisture and self-oxidization due to contact with fingers. However this test chip is to be dipped in sample liquid such as urine and is not directed to automated handling unlike the chemical analysis film chip of the present invention.

The chemical analysis element disclosed in the latter publication is a multi-layer analysis element comprising a support sheet, a reagent layer and a porous medium and is used in the form of tape in a continuous length, sheet or strip.

In the publication, though there are descriptions that the analysis element in the form of tape is fed and taken up and that an analysis element in the form of a small sheet is transferred on a support card, there is no description that a film chip for one analysis is transferred as the chemical analysis film chip of the present invention.

DESCRIPTION OF THE PREFERRED EMBODIMENT

FIG. 1A shows a chemical analysis film chip 1 in accordance with an embodiment of the present invention under the normal humidity condition and FIGS. 1B and 1C show the state of the chemical analysis film chip 1 in a dry state.

The film chip 1 is prepared by coating a reagent layer 3 on a transparent support sheet 2 which is formed of polyethylene terephthalate sheet or polystyrene sheet, and integrally laminating a spreading layer 4 on the reagent layer 3. It should be noted that the film chip 1 is not provided with any frame.

The reagent layer 3 comprises at least one layer composed of a hydrophilic polymer binder such as gelatin containing therein a reagent component which makes coloring reaction with analyte.

The spreading layer 4 is formed of woven or knitted fabric (or cloth) of synthetic fiber resistant to rubbing such as polyester, or of blend of natural fiber and synthetic fiber, unwoven fabric or paper and functions as a protective layer. Further the spreading layer 4 causes sample liquid spotted thereon to uniformly spread over the reagent layer 3.

The thickness of the support sheet 2 is, for instance 150 to 200 $\mu$m, the thickness of the reagent layer 3 is, for instance 10 to 40 $\mu$m, and the thickness of the spreading layer 4 is, for instance 200 to 250 $\mu$m.

The support sheet 2, the reagent layer 3 and the spreading layer 4 are of substantially the same size and for instance 12 mm×12 mm.

Under the normal humidity conditions the film chip 1 is substantially flat as shown in FIG. 1A. The film chip 1 is stored in a dry environment (e.g., in an environment where the humidity is not higher than 20%) in order to suppress chemical reaction, and in a dry state, the film chip 1 is curled (or warped or curved) toward the spreading layer 4 as shown in FIG. 1B or 1C. In the state shown in FIG. 1B, the film chip 1 is curled in one direction and in the state shown in FIG. 1C, the film chip 1 is curled in a plurality of directions.

The direction of curl and the curvature thereof varies depending on the kind of the reagent in the reagent layer 3, the arrangement of the layers and the kind of material of the support sheet 2. For example, when a film chip 1 which is 12 mm×12 mm in size and 0.5 mm in thickness is stored in an absolute dry state for five days, the curvature is about 100 to 1500 $\mu$m at the maximum.

It is difficult for the conventional automatic chemical analysis system as it is to handle the curled film chip 1. That is, operation of taking out the film chips 1 one by one from a cartridge in the drying container (supplier), operation of spotting sample liquid on the film chip 1 and transferring it to the incubator, operation of inserting the film chip 1 into the cell of the incubator and incubating it at a constant temperature and operation of measuring the optical density after a predetermined time and taking out and discarding the film chip 1 are must be carried out taking into account the shape of the film chip 1.

Automatic operation of biochemical analysis using the curled dry chemical analysis film chip 1 will be described hereinbelow.

Figure 2:
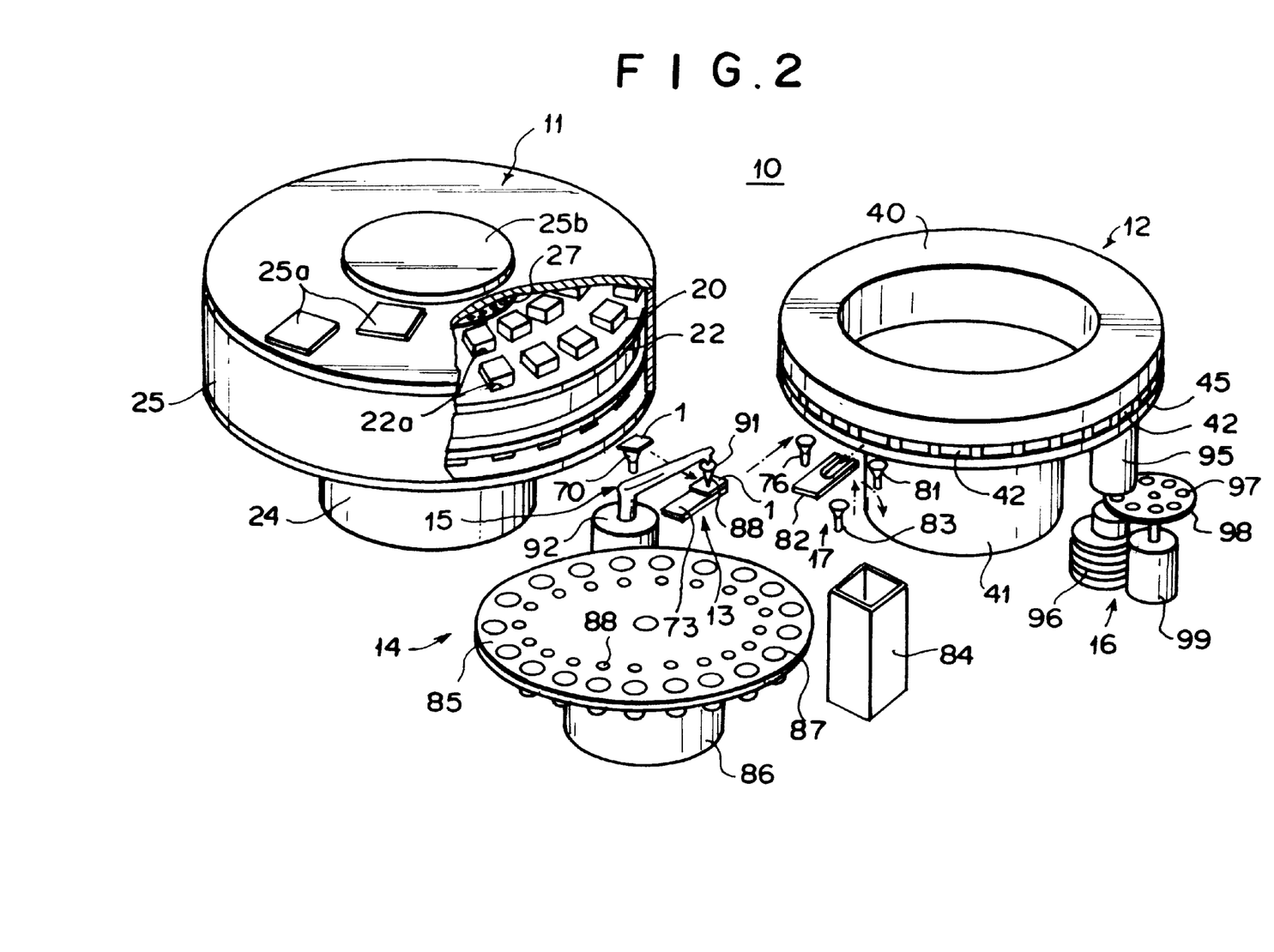
FIG. 2 is a schematic perspective view showing an biochemical analysis system for effecting biochemical analysis using the dry chemical analysis film chip of the present invention.

FIG. 2 shows an example of a biochemical analysis system 10 which automatically handles the chemical analysis film chip 1.

The biochemical analysis system 10 comprises a film supplier 11 in which a plurality of rectangular dry film chips 1 are stored, an incubator 12 which is disposed beside the film supplier 11 and incubates the film chips 1 transferred from the film supplier 11, a film transfer means 13 which transfers the film chips 1 from the film supplier 11 to the incubator 12, a sample liquid supplier 14 in which a plurality of sample liquids such as serum, urine or the like are stored, an spotting means 15 which spots one of the sample liquids in the sample liquid supplier 14 onto the film chips 1 on the way to the incubator 12, and a light measuring system 16 disposed below the incubator 12.

Figure 3A:
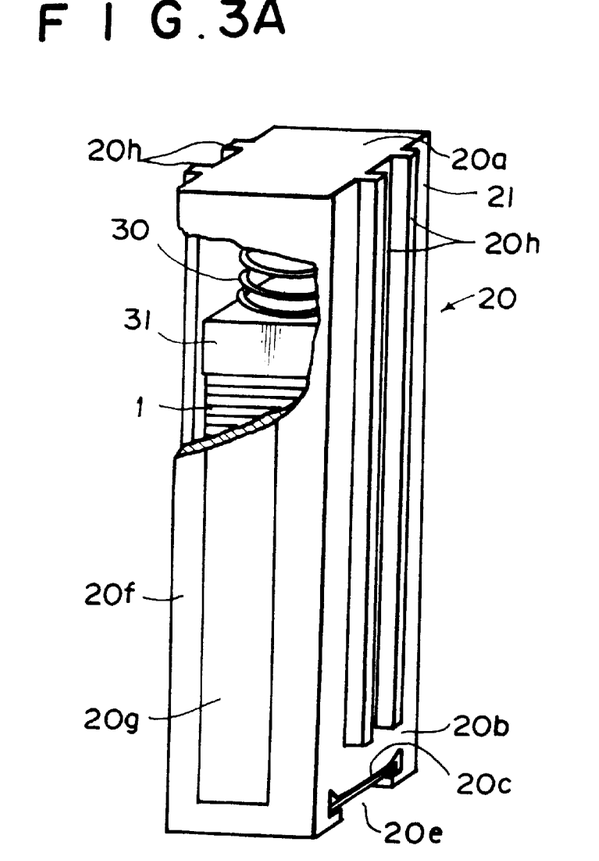
FIG. 3A is a perspective view partly cut away showing the cartridge.

The film chips 1 are stored in cartridges 20 (FIG. 3) for the respective terms of analysis. In the cartridge 20, a plurality of the film chips 1 are stacked with the support sheet 2 facing downward. As shown in FIG. 2, the film supplier 11 is provided with a plurality of cartridge holding portions 22a which are arranged in inner and outer circles on a disk-like support 22 and a plurality of cartridges 20 loaded with the film chips 1 are held in the respective cartridge holding portions 22a. The support 22 is supported for rotation on a base portion 24 and is rotated by a motor not shown so that a predetermined cartridge holding portion 22a is brought to a film takeout position where the film transfer means 13 takes out a film chip 1 from the cartridge 20.

The support 22 is provided with a cover 25 which encloses inner space of the film supplier 11. The cover 25 is provided with a pair of openings 25a provided with lids and the cartridges 20 can be taken out and inserted into the cartridge holding portion 22a through the openings 25a. An dehumidifying agent holding portion 27 is formed in the support 22 at the center thereof and dehumidifying agent (or desicative agent) is loaded in the dehumidifying agent holding portion 27 through an opening 25b formed in the cover 25. The opening 25b is provided with a lid. Thus the inner space of the film supplier 11 is kept dry. A shutter (not shown) is provided in the lower surface of the cover 25 in the film takeout position. The shutter is opened when the film chip 1 is taken out from the cartridge 20 and a suction pad 70 of the film transfer means 13 takes out the lowermost film 1 in the cartridge 20 through the shutter.

The cartridge 20 will be described in detail hereinbelow as well as the operation of taking out the film chip 1 from the cartridge 20.

Figure 3B:
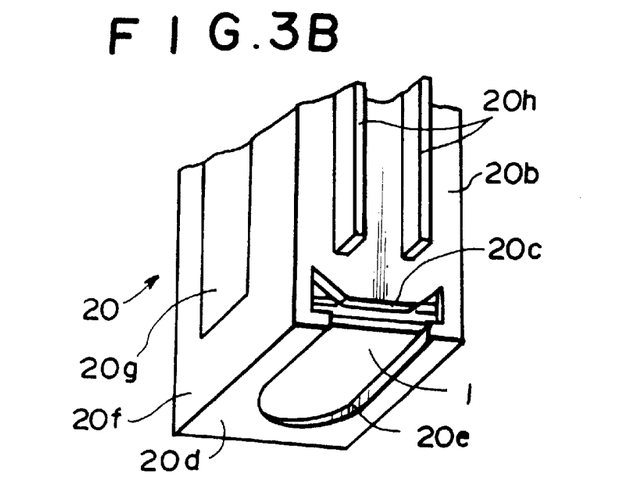
FIG. 3B is a fragmentary perspective showing a bottom portion of the cartridge.

FIG. 3A is a perspective view partly cut away showing the cartridge 20 and FIG. 3B is a fragmentary perspective view showing the bottom of the cartridge 20. The cartridge 20 comprises a box-like casing 21 for accommodating a stack of film chips 1, a spring member 30 mounted on the inner side of the top wall 20a of the casing 21 and a pushing member 31 which is mounted on the lower end portion of the spring member 30 and urges downward the stack of the film chips 1. A first opening 20c is formed in one side wall 20b of the casing 21 at a portion near to the bottom wall 20d of the casing 21. The first opening 20c is shaped and sized to permit only the lowermost film chip of the stack to pass therethrough. A U-shaped second opening 20e which gives a suction pad (suction cup) 70 for holding the film chip 1 access to the lowermost film chip is formed in the bottom wall 20d of the casing 21.

On the outer surface of a side wall 20f of the casing 21, there is recorded magnetic stripes (or a magnetic band) 20g which carries information such as properties of the film chips 1 accommodated in the cartridge 20. A pair of ribs 20h are formed in each of the side wall 20b and the side wall opposite to the side wall 20b in order to hold the cartridge 20 in the cartridge holding portions 22a and to prevent insertion of the cartridge 20 in a wrong position.

A plurality of (e.g., 100 pieces) film chips 1 are stacked with the support sheet facing downward and set between the pushing member 31 and the bottom wall 20d of the casing 21.

Figure 4A:
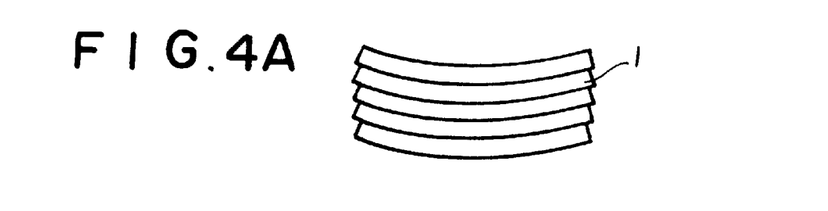
FIG. 4A and 4B are schematic views showing the stack of the chemical analysis film chips in the cartridge.
Figure 4B:
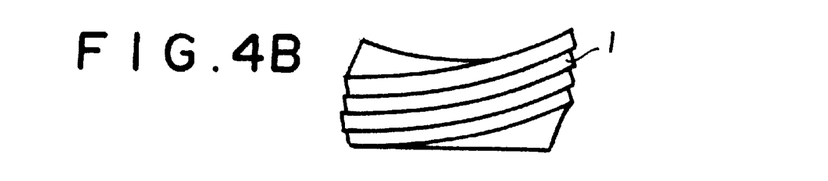

Since the film chips 1 are curled toward the spreading layer 4 in the dry state, they are stacked in the cartridge 20 in a state as shown in FIG. 4A or 4B.

The bottom wall 20d of the casing 21 is removable from the side walls of the casing 21 and is inserted into the side walls with the stack of the film chips 1 placed thereon so that the uppermost film chip is pressed against the pushing member 31. The bottom wall 20d is fixed there by a suitable means (not shown).

The casing 21 is, for instance, 15 mm×15 mm×100 mm in size and about 1 mm in wall thickness. The casing 21 may be formed of, for instance, light-shielding black ABS resin.

Information on the film chips 1 in the cartridge such as those representing the kind of the film chips 1, the terms of analysis, the number of the film chips and the like are magnetically recorded on the magnetic stripes 2g, and a magnetic head in the analysis system reads the information for the subsequent biochemical analysis.

How to take out the film chips 1 from the cartridge will be described with reference to FIGS. 5A to 5D and 6A and 6B, hereinbelow.

Figure 5A:
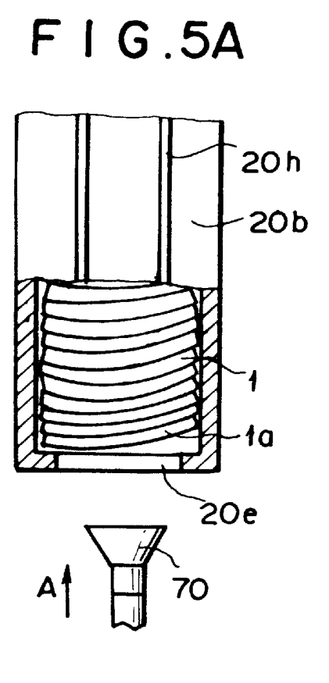
FIGS. 5A to 5D are schematic views for illustrating the procedure of taking the film chip from the cartridge.

As shown in FIG. 5A, the film chips 1 are stacked in the cartridge 20 with each of the film chips 1 curled to be convex downward and the stack is pressed against the upper surface of the bottom wall 20d under the force of the spring member 30. The spring force of the spring member 30 is set so that, even after all the film chips 1 but one are taken out from the cartridge 20, the spring member 30 can press the last film chip 1 against the upper surface of the bottom wall 20d.

The suction pad 70 for taking out the film chip 1 is positioned below the second opening 20e of the casing 21 and is moved upward under the control of a controller.

Figure 5B:
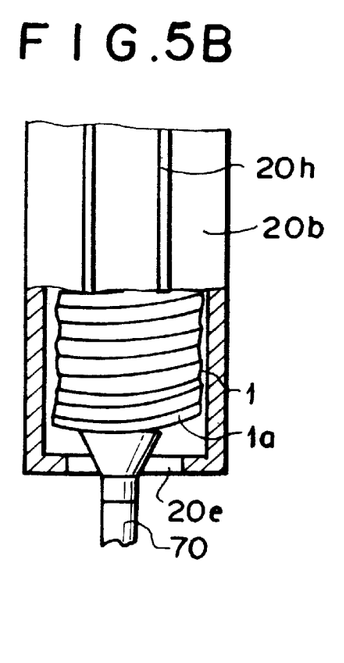

The suction pad 70 is inserted through the second opening 20e to be brought into abutment against the lowermost film chip 1a and further moved upward into closer contact with the lowermost film chip 1a as shown in FIG. 5B. In this position, the suction pad 70 holds the lowermost film chip 1 under a suction force supplied from a vacuum pump not shown. Since the suction pad 70 attracts the support sheet 2 of the film chip 1a, the film chip 1a can be surely attracted on the suction pad 70 under the suction force and there is no possibility of damaging the reagent layer 3 and/or spreading layer 4.

The support sheet 2 is arranged to be strong enough to withstand the suction force acting on the film chip 1 during taking out from the cartridge 20 and during subsequent transfer thereof.

Figure 5C:
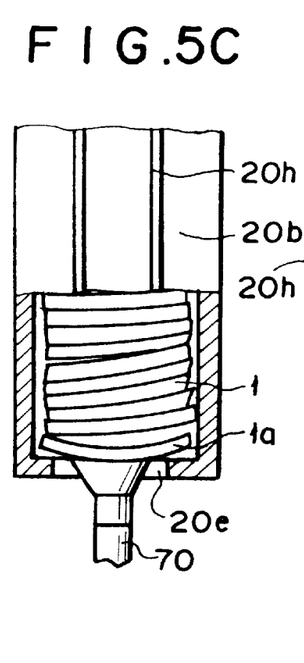

Thereafter the suction pad 70 is moved downward holding the film chip 1a under the control of the controller until the film chip 1a is reshaped into the predetermined warped-shape convex downward as shown in FIG. 5C. That is, the parts of the film chip 1a on opposite sides of the suction pad 70 is brought into abutment against the edges of the second opening 20e on the way, and as the suction pad 70 is further moved downward, the central portion of the film chip 1a is pulled downward with the parts of the film chip 1a on opposite sides of the suction pad 70 supported by the edges of the second opening 20e, whereby the film chip 1a is reshaped into the predetermined warped-shape.

The suction force applied to the support sheet 2 during the reshaping is about 10 g to about 200 g and preferably about 50 g to 100 g assuming that the film chip 1a is 12 mm×12 mm in size.

The reason why the film chip 1a is reshaped into the predetermined warped-shape is that the film chips 1 in the cartridge 20 are warped or curled in different curvatures and in different shapes and since the first opening 20c is shaped and sized to permit only one film chip 1 to pass therethrough, the film chip 1 cannot be passed through the first opening 20c unless its shape and curvature conform to the shape of the first opening 20c.

Figure 6A:
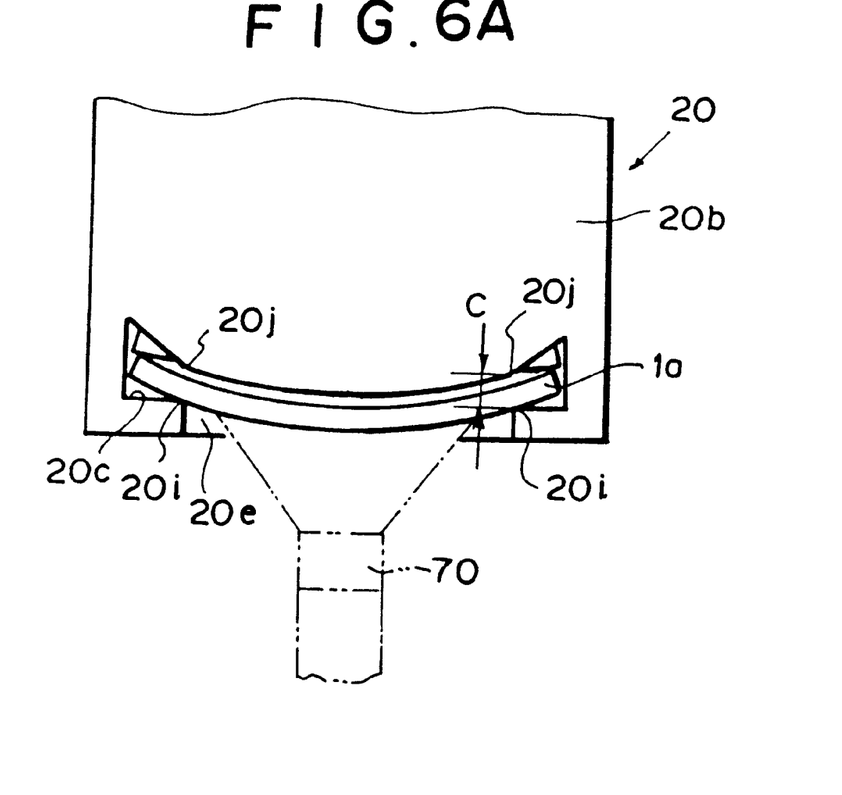
FIGS. 6A and 6B are views for illustrating the relative position of the film chip and the film takeout slit of the cartridge.

As shown in FIG. 6A, the width of the first opening 20c between the edge 20i of the the second opening 20e against which the film chip 1a is brought into abutment during reshaping and the edge 20j of the first opening 20c above the edge 20i is set to be larger than the thickness of the film chip 1a and smaller than the double of the thickness of the film chip 1a. The width of the first opening 20c is relatively large at the other part so that the film chip 1a can be smoothly passed therethrough.

Figure 6B:
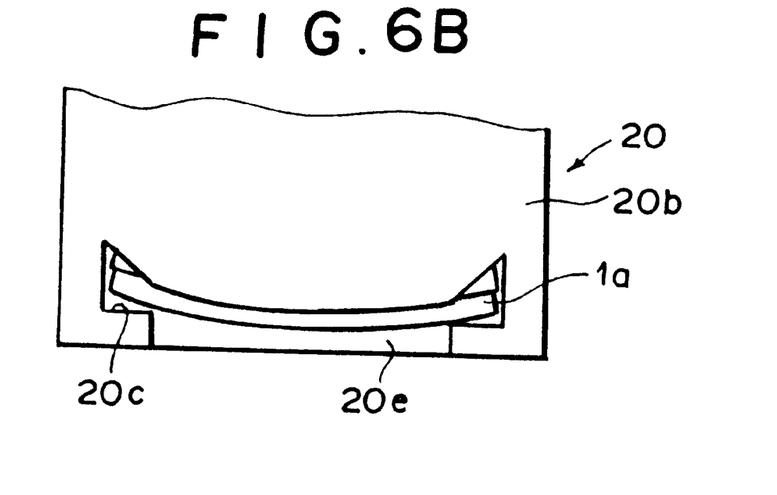

In the state where the film chip 1 is not reshaped, a part of the edge of the film chip 1a interferes with the inner surface of the side wall 20b above the first opening 20c to prevent the film chip 1a from passing through the first opening 20c as shown in FIG. 6B. Accordingly the film chip 1a cannot fall off the cartridge 20, for instance, during transfer of the cartridge 20.

Figure 5D:
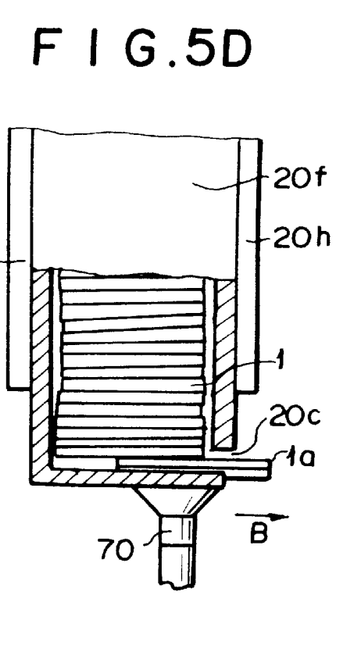

After reshaping, the suction pad 70 is moved in the direction of arrow B to take out the film chip 1a through the first opening 20c as shown in FIG. 5D.

When the lowermost film chip 1a is taken out, the spreading layer 4 of the lowermost film chip 1 is rubbed with the support sheet 2 of the second lowermost film chip 1, and accordingly it is preferred that the friction coefficient between the spreading layer 4 and the support sheet 2 be small (e.g., not larger than 1).

After the lowermost film chip 1a is taken out, the stack of the film chips 1 are moved downward under the force of the spring member 30 by the distance corresponding to the thickness of the film chip 1.

As shown in FIG. 2, the incubator 12 comprises a disk-like body portion 40 which is supported to be rotated by a drive mechanism 41 disposed below the body portion 40 at the center thereof. A plurality of cells 42 are provided in the body portion 40 at predetermined intervals in the circumferential direction thereof. The film chips 1 are incubated in the cells 42.

The body portion 40 comprises a lower disk 45 having a flat upper surface and an upper disk (not shown) provided on the lower disk 45 and is fixed to the lower disk 45 by screws. The peripheral edge portion of the upper disk is bulged upward to form an annular channel open downward. The lower edge of the outer peripheral edge of the upper disk is spaced from the upper surface of the lower disk 45 to form an opening which opens in the side surface of the incubator 12 and gives access to the cells 42. A heater (not shown) is disposed between the lower and upper disks and the disks are formed of metal. The heater is controlled to heat the film chips 1 in the cells 42 to a predetermined temperature (e.g., 37° C.) on the basis of the output of a temperature sensor (not shown).

A plurality of light measuring windows for photometry are formed in the lower disk 45 to be opposed to the respective cells 42, and a film retainer (or a cover) 61 (FIG. 7) for fixing the film chip 1 in a predetermined position in the cell 42 is provided above each of the light measuring windows. A measuring system 16 has a light measuring head 95 which is disposed below the body portion 40 in a light measuring position.

Figure 7:
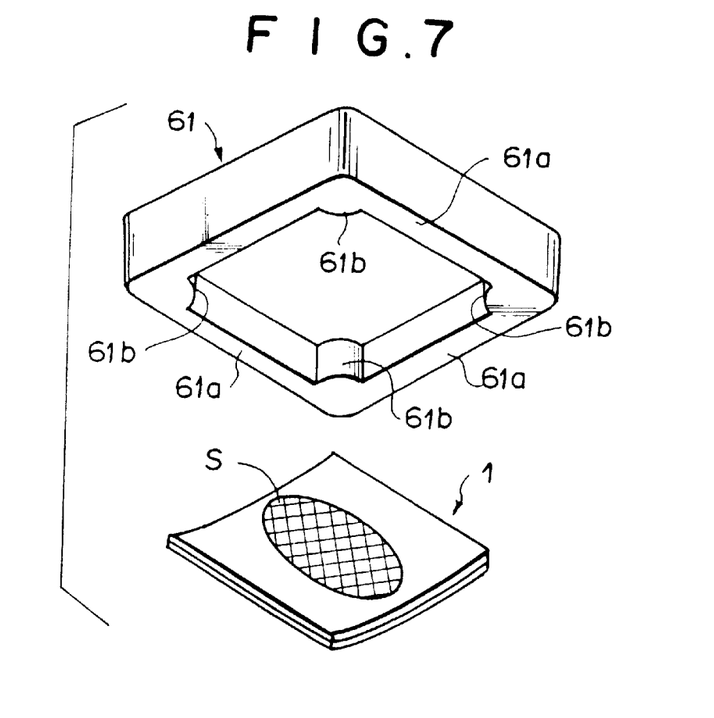
FIG. 7 is a schematic perspective view showing the film retainer in the cell of the incubator.

As shown in FIG. 7, the film retainer 61 has a rectangular frame portion 61a on the lower surface thereof. The inner dimensions of the frame portion 61a is larger than the outer dimensions of the film chip 1 and a protrusion 61b is provided at each corner of the frame portion 61a to project inward. When the film retainer 61 is moved downward against the film chip 1, only the protrusions 61b are brought into contact with the film chip 1 so that the retainer 61 is not brought into contact with the portion S over which the sample liquid can spread. The film retainer 61 is urged downward under the force of a spring provided on the upper surface of the retainer 61.

Thus the film chip 1 is kept flat during incubation and measurement of the optical density, whereby incubation can be effected with a high efficiency and the accuracy of analysis can be ensured.

The film transfer means 13 for transferring the film chip 1 from the film supplier 11 to the incubator 12 comprises said suction pad 70 for taking out the film chip 1 from the cartridge 20, a horseshoe-like transfer member 73 which receives the film chip 1 held on the suction pad 70 from below the film chip 1 with the reagent layer 3 facing upward and inserts the film chip 1 into the cell 42 in the incubator 12 through the opening which opens sideways, and a suction member 76 which moves in and out the cell 42 from below the cell and receives the film chip 1 held by the transfer member 73 inside the cell 42.

The suction pad 70 comprises a suction cup which is directed upward and attracts the lower side of the support sheet 2 of the film chip 1. The suction cap is supported on a base portion which is moved back and forth and up and down by a drive mechanism (not shown) and is connected to a suction pump (not shown) through a vacuum tube.

The suction pad 70 takes out the film chip 1 from the cartridge 20 in the manner described above and transfers the film chip 1 to the position where the sample liquid is spotted onto the film chip 1.

Figure 8:
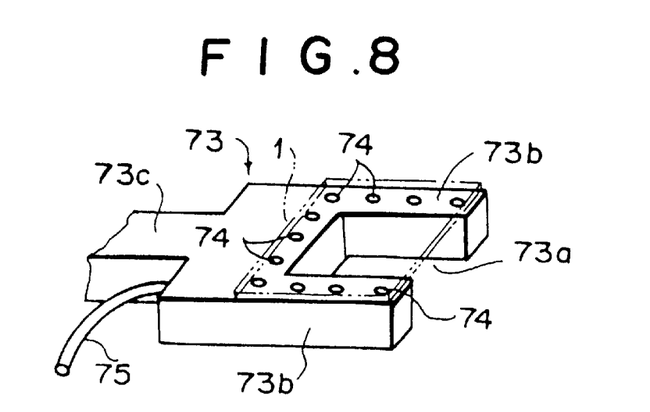
FIG. 8 is a perspective view showing the transfer member.

As shown in FIG. 8, the transfer member 73 is like a horseshoe in shape and has a flat upper surface. That is, the transfer member 73 is bifurcated in the front end portion to form a pair of arm portions 73b extending on opposite sides of a cutaway portion 73a, and a plurality of suction holes 74 are formed to surround the cutaway portion 73a and to open in the upper surface of the transfer member 73. The suction holes 74 are connected to a suction pump (not shown) through a vacuum tube 75. The base portion 73c of the transfer member 73 is connected to a drive mechanism (not shown) to be inserted into the cell 42 in the incubator 12 through the side opening of the incubator 42.

When the transfer member 73 receives the film chip 1 from the suction pad 70, the transfer member 73 is moved toward the suction pad 70 holding the film chip 1 and is stopped in a position where the suction pad 70 is in the cutaway portion 73a of the transfer member 73 with the film chip 1 positioned above the cutaway portion 73a. Then the suction pad 70 is moved downward below the transfer member 73 leaving the film chip 1 on the transfer member 73. The film chip 1 left on the transfer member 73 is held thereon under the suction force provided through the suction holes 74. When the position of the suction pad 70 relative to the film chip 1 held thereby is accurately controlled, the position of the transfer member 73 relative to the film chip 1 can be accurately controlled and a predetermined amount of the sample liquid can be accurately spotted onto the center of the reagent layer 3 of the film chip 1 held by the transfer member 73.

The suction member 76 is positioned below the cell 42 in the incubator 12 and comprises a suction cup supported on a base portion (not shown) to be moved up and down by a drive mechanism not shown) into and away from the cell 42 through the light measuring window. The suction cup is connected to a suction pump (not shown) through a vacuum hose.

A film takeout means 17 is disposed in the film takeout position of the incubator 12. The film takeout means 17 comprises a takeout suction pad 81 which attracts the film chip 1 in the cell 42 which has finished with measurement and lifts it, a horseshoe-like transfer member 82 which receives the film chip 1 from the takeout suction pad 81 and transfers it outside the incubator 12 and a discarding suction pad 83 which receives the film chip 1 from the transfer member 82 and discards it into a discarding box 84.

The sample liquid supplier 14 comprises a turn table 85 which is rotated by a drive mechanism 86. The turn table 85 holds a plurality of sample tubes 87 filled with sample liquids which are arranged along the circumferential edge of the turn table 85 and is rotated to bring the sample tubes 87 to a sample liquid supplying position one by one. A plurality of nozzle tips 88 which are mounted on an spotting nozzle 91 to be described later are held on the turn table 85 inside the sample tubes 87.

The spotting means 15 for spotting the sample liquid onto the film chip 1 comprises an spotting nozzle 91 which sucks and discharges the sample liquid, and a nozzle tip 88 like a pipette is demountably mounted on the nozzle 91. The nozzle 91 is moved up and down and rotated by a drive mechanism 92. That is, the nozzle 91 sucks the sample liquid from the sample liquid supplier 14, is moved to the film chip 1 held by the transfer member 73, and then spots the sample liquid onto the film chip 1. The nozzle tip 88 is changed every time the sample liquid is changed.

The film chip 1 spotted with the sample liquid is transferred to the incubator 12 and incubated there. After incubation for a predetermined time, the optical density of the reagent layer 3 is measured by the light measuring system 16 disposed below the incubator 12. The light measuring system 16 comprises said light measuring head 95 for measuring the optical density of the color formed by the coloring reaction between the reagent layer 3 and the sample liquid. The light measuring head 95 projects measuring light containing light of a predetermined wavelength onto the reagent layer 3 through the support sheet 2 and detects reflected light with a photodetector. Light from a light source (lamp) 96 enters the light measuring head 95 through a filter 97 and is caused to impinge upon the reagent layer 3 by the head 95. A plurality of kinds of the filters 97 are mounted on a rotary disk 98 which is driven by an electric motor 99 and one of the filters 97 is selected according to the term of measurement.

The reflected light from the reagent layer 3 carries thereon optical information (more particularly the amount of light) on the amount of coloring matter formed by the coloring reaction between the reagent layer 3 and the sample liquid. The reflected light is received by the photodetector and the optical information carried by the reflected light is converted to an electric signal by the photodetector. The electric signal is input into a determination section through an amplifier. The determination section determines the optical density of the coloring matter formed by the coloring reaction between the reagent layer 3 and the sample liquid on the basis of the level of the electric signal and determines the concentration of a predetermined chemical component in the sample liquid.

The measurement by the biochemical analysis system 10 is effected in the following manner. That is, a film chip 1 is taken out by the suction pad 70 of the transfer means 13 from a cartridge 20 storing therein chemical analysis film chips 1 corresponding to the term of measurement. The film chip 1 held by the suction pad 70 is transferred to the transfer member 73 with the reagent layer 3 facing upward and a sample liquid is spotted onto the reagent layer 3.

That is, a nozzle tip 88 is mounted on the spotting nozzle 91 of the spotting means 15 and the spotting nozzle 91 is moved above a desired sample tube 87 in the sample liquid supplier 14. Then the nozzle 91 is moved downward to bring the nozzle tip 88 into the sample liquid and the nozzle 91 sucks a predetermined amount of the sample liquid into the nozzle tip 88. Thereafter the nozzle 91 is moved above the center of the film chip 1 on the transfer member 73 and moved downward toward the film chip 1, where a predetermined amount of sample liquid is spotted onto the reagent layer 3 from the nozzle tip 88. The sample liquid spreads over the reagent layer 3 and mixes with the reagent therein.

The film chip 1 spotted with the sample liquid is inserted into one of the cells 42 of the incubator 12 through the side opening by the transfer member 73.

Coloring reaction (coloring matter forming reaction) is caused when the film chip 1 with the sample liquid is heated to a predetermined temperature in the cell 42 in the incubator 12, and the optical density of the coloring matter is measured by the light measuring head 95 after a predetermined time or at predetermined intervals.

The dry chemical analysis film chip of the present invention need not be limited to those described above but may be variously modified.

For example, though, in the above embodiment, the film chip comprises three layers, the support sheet, the reagent layer and the spreading layer, the film chip may comprise a support sheet, a water absorbing layer having a hydrophilic polymer as a major component and a reagent-containing spreading layer or support sheet and a reagent-containing porous layer.

Further the automatic biochemical analysis system for carrying out biochemical analysis using the chemical analysis film chip of the present invention need not be limited to that described above but may be variously modified so long as it can carry out biochemical analysis with a high accuracy without damaging the film chip.

What is claimed:

1. A method of analysis of a chemical component contained in a fluid, which comprises:
   a) providing a plurality of frameless dry chemical analysis film chips, the chips consisting essentially of, superposed in this order, a support sheet and at least one reagent layer and an outermost layer formed on the support sheet, the layers arranged to warp in a dry atmosphere having a humidity of not higher than 20%, stacked in a cartridge;
   b) removing a single chip from the cartridge by applying suction to the chip;
   c) applying the fluid to the removed chip, the fluid being applied to the outermost layer of the film chip;
   d) incubating the film chip from step c at a predetermined temperature for a predetermined time; and
   e) measuring the optical density of the incubated chip.

2. The method of claim 1, in which the support sheet has sufficient strength to permit transfer of the chemical analysis film chip while being held by suction.

3. The method of claim 2 in which the support sheet, the reagent layer and the outermost layer are all strong enough to withstand a suction force acting on the film chip during transfer thereof without being damaged.

4. The method of claims 1, 2 or 3, in which the outermost layer is a spreading layer.

5. The method of claim 4, in which the spreading layer has sufficient strength to withstand rubbing with a member handling the film chip or with a support sheet of another film chip.

6. The method of claim 5, in which the spreading layer is a fabric.

7. The method of claim 5, in which the spreading layer is paper.

8. The method of claims 1, 2 or 3 in which the outermost layer has sufficient strength to withstand rubbing with a member handling the film chip or with a support sheet of another film chip.

9. The method of claim 8, in which the outermost layer is a fabric.

10. The method of claim 8, in which the outermost layer is paper.

11. A method of analysis of a chemical component contained in a fluid, which comprises:
   a) providing a plurality of dry chemical analysis film chips, the chips consisting essentially of, superposed in this order, a support sheet, a water absorbing layer having a hydrophilic polymer and a porous outermost layer containing therein a reagent, which are formed on the support sheet and arranged to warp in a dry atmosphere having a humidity of not higher than 20%, stacked in a cartridge;
   b) removing a single chip from the cartridge by applying suction to the chip;
   c) applying the fluid to the removed chip, the application of the fluid being to the outermost layer of the film chip;
   d) incubating the film chip to which the fluid has been applied at a predetermined temperature for a predetermined time; and
   e) measuring the optical density of the incubated chip.

12. The method of claim 11, in which the support sheet has a strength to permit transfer of the chemical analysis film ship while holding it under a suction force.

13. The method of claim 12, in which the support sheet and the outermost layer are both strong enough to withstand a suction force acting on the film chip during transfer thereof without being damaged.

14. The method of any one of claims 11, 12, and 13, in which the outermost layer is a spreading layer.

15. The method of claim 14, in which the spreading layer has sufficient strength to withstand rubbing with a member handling the film chip or with the support sheet of another film chip.

16. The method of claim 15, in which the spreading layer is fabric.

17. The method of any one of claims 11, 12, and 13, in which the outermost layer has a strength to withstand rubbing with a member handling the film chip or with a support sheet of another film chip.

18. The method of claim 17, in which the outermost layer is fabric.

19. The method of claim 17, in which the outermost layer is paper.

20. A method of analysis of a chemical component contained in a fluid, which comprises:
   a) providing a plurality of dry chemical analysis film chips, the chips consisting essentially of, support sheet and a porous layer containing therein a reagent formed on the support sheet and arranged to warp in an atmosphere having a humidity of not higher than 20%, stacked in a cartridge;
   b) removing a single chip from the cartridge by applying suction to the chip;
   c) applying the fluid to the removed chip, the application of the fluid being to the porous layer of the film chip;
   d) incubating the film chip to which the fluid has been applied at a predetermined temperature for a predetermined time; and
   e) measuring the optical density of the incubated chip.

21. The method of claim 20, in which the support sheet has sufficient strength to permit transfer of the chemical analysis film ship while holding it under suction.

22. The method of claim 21, in which the support sheet and the porous layer are both strong enough to withstand a suction force acting on the film chip during transfer thereof without being damaged.

23. The method of any one of claims 20, 21, and 22, in which the porous layer has the strength to withstand rubbing with a member handling the film chip or with the support sheet of another film chip.

24. The method of claim 23, in which the porous layer is fabric.

25. The method of claim 23, in which the porous layer is paper.

* * * * *